(12) United States Patent
Chbat et al.

(10) Patent No.: US 8,521,556 B2
(45) Date of Patent: Aug. 27, 2013

(54) INTEGRATION OF PHYSIOLOGICAL MODELS IN MEDICAL DECISION SUPPORT SYSTEMS

(75) Inventors: Nicolas Chbat, White Plains, NY (US); William Lord, Fishkill, NY (US)

(73) Assignee: Koninklijke Philips N.V., Eindhoven (NL)

( * ) Notice: Subject to any disclaimer, the term of this patent is extended or adjusted under 35 U.S.C. 154(b) by 128 days.

(21) Appl. No.: 12/747,545

(22) PCT Filed: Dec. 9, 2008

(86) PCT No.: PCT/IB2008/055183
§ 371 (c)(1),
(2), (4) Date: Aug. 24, 2010

(87) PCT Pub. No.: WO2009/081304
PCT Pub. Date: Jul. 2, 2009

(65) Prior Publication Data
US 2010/0332249 A1    Dec. 30, 2010

Related U.S. Application Data

(60) Provisional application No. 61/014,588, filed on Dec. 18, 2007.

(51) Int. Cl.
*G06Q 10/00*    (2006.01)
(52) U.S. Cl.
USPC .................................................. 705/2; 703/11
(58) Field of Classification Search
USPC ............................................................ 705/2
See application file for complete search history.

(56) References Cited

U.S. PATENT DOCUMENTS

| | | |
|---|---|---|
| 2004/0158163 A1 | 8/2004 | Cohen et al. |
| 2009/0150134 A1* | 6/2009 | De Leon et al. ................. 703/11 |

FOREIGN PATENT DOCUMENTS

| | | |
|---|---|---|
| EP | 1746558 A2 | 1/2007 |
| EP | 1788540 A1 | 5/2007 |
| WO | 2004023977 A2 | 3/2004 |

OTHER PUBLICATIONS

K. Lu, J. W. Clark, F.H. Ghobel, D. L. Ware, J. B. Zwischenberger, and A. Bidan; Whole-Body Gas Exchange in Human Predicted by a Cardiopulmonary model, Mar. 2002(2003),Cardivascular engineering: An international Journal, vol. 3, No. 1.*

Kuipers, "Reasoning With Qualitative Models", Artificial Intelligence, vol. 59, 1993, p. 125-132.

Fitz-Clarke, "Computer Simulation of Human Breath-Hold Diving: Cardiovascular Adjustments", Eur. J. Appl. Physiol, (2007), 100: 207-224.

(Continued)

*Primary Examiner* — Hiep V Nguyen

(57) ABSTRACT

When generating a model of physiological systems in a patient, differential equations representing parameters and variables in the systems are linked together to form one or more sub-models (e.g., one for each physiological system), which in turn are linked together to form the patient model. Simulations of hypothetical clinical situations are then run on the model to solve for the variables, and the solutions are output as decision support data for review by a clinician to facilitate a determination of a treatment of diagnosis for the patient. Additionally, model predictions can be compared to actual measurements, when available, and the model can be refined or optimized as a function of the comparison.

19 Claims, 8 Drawing Sheets

(56) References Cited

OTHER PUBLICATIONS

Woodruff et al, "A Model for the Design and Evaluation of Algorithms for Closed-Loop Cardiovascular Therapy", IEEE Transactions on Biomedical Engineering, vol. 44, No. 8, Aug. 1997.

Lu et al, "Whole-Body Gas Exchange in Human Predicted by a Cardiopulmonary Model", Cardiovasculalr Engineering, vol. 4, No. 1, Mar. 2002, p. 1-19.

* cited by examiner

INTEGRATION OF PHYSIOLOGICAL MODELS IN MEDICAL DECISION SUPPORT SYSTEMS

The present application finds particular utility in clinical patient modeling systems, and other clinical simulation devices or techniques. However, it will be appreciated that the described technique(s) may also find application in other types of modeling systems and/or other simulation systems or techniques.

Conventional systems and methods for physiological modeling for clinical usage have several drawbacks. For instance, physiologists, engineers, and other scientists have developed physiological models mathematically describing single physiological systems. However, describing interactions of two or a few physiological systems has proven elusive (in terms of applicability). Other known models are based on available patient data, and hence they are statistical or probabilistic approaches. Typically, mathematical models describing different physiological systems are developed and validated without regard to an eventual implementation in a medical system to be used in the medical domain.

Volume pumped by the heart is often equated to the blood flow out of the left ventricle. This quantity is also termed "cardiac output" (CO) and is an important measure in the assessment of hemodynamic conditions. As early as 1870, Adolph Fick laid out a method to measure this quantity, and subsequent methods have been attempted ever since. Such methods include: direct Fick, indirect Fick (or $CO_2$ rebreathing), thermodilution, lithium dilution, pulse pressure waveform analysis, esophageal Doppler ultrasonography, transesophageal echocardiography, thoracic electrical bioimpedence, partial $CO_2$ rebreathing, acetylene rebreathing, and open-circuit wash-in of acetylene. All of the aforementioned methods to estimate CO are invasive to the patient. They vary from inhalation or injection of a fluid, typically an inert gas, to placing uncomfortable probes at different locations in and on the body.

Three main problems are commonly encountered when employing these methods. For example, accuracy of the CO estimate suffers due to the possible inherent inaccuracies in fluid inhalation in terms of diffusive and reactive losses with unintended organs and tissues. Additionally, bulk body motion can adversely affect probe positioning. Moreover, clinical complications (infections, etc.) due to probe-body interaction, for instance in the case of a Swan-Ganz catheter, can produce undesirable effects.

Thus, there is an unmet need in the art for systems and methods that facilitate overcoming the deficiencies described above.

In accordance with one aspect, a computer-readable medium comprises a program that is configured to emulate cardiopulmonary function of a human, the program comprising means for providing a generic model of the cardiopulmonary system of the patient, said model including pulmonary circulation, systemic circulation, 4-heart chambers, autonomic nervous system, metabolism, gas exchange, lung mechanism, and reflex, and means for measuring cardiopulmonary variables of the human. The program further includes instructions for displaying relevant cardiopulmonary variables that are reflective of a current health condition of the human, and simulating functioning of the cardiopulmonary system.

In accordance with another aspect, a program embodied on a computer readable medium that is configured to emulate the cardiopulmonary functioning of a human comprises means for providing a generic model of the cardiopulmonary system of the human, means for measuring cardiopulmonary variables of the human, and means for iteratively changing cardiopulmonary parameters of the model in order for cardiopulmonary variables of the generic model to reflect the cardiopulmonary variables of the human.

In accordance with another aspect, a clinical patient modeling system, including a pre-generated physiological model of a patient, comprising at least one sub-model of a physiological system in a patient with a plurality of differential equations that describe relationships among physiological parameters and variables relevant to the physiological system, and a model generator that receives patient data, inserts the patient data into the physiological model, and outputs decision support data for consideration by a user when diagnosing or treating the patient. The system further includes a user interface into which the user inputs one or more parameters to adapt the model to a hypothetical situation into which the user is considering placing a patient.

Yet another aspect relates to a method of evaluating hypothetical clinical scenarios, including generating a model from physiological data gleaned from a patient population, representing the physiological data in the model as differential equations that describe parameters and variables associated with a patient, adjusting parameters in the model to adapt the model for a hypothetical situation into which the patient is to be placed, and running a simulation on the model to generate decision support data and solve for the variables in the model.

One advantage is that resides in model representation and/or model-linking to more than one physiological system.

Another advantage is that several variables are solved for and output as decision support data.

Another advantage resides in outputting solutions for clinically relevant variables.

Another advantage relates to predicting (computing) values that are hard to measure or even immeasurable.

Yet another advantage relates to predicting values for clinically relevant physiological variables.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

Figure 1:
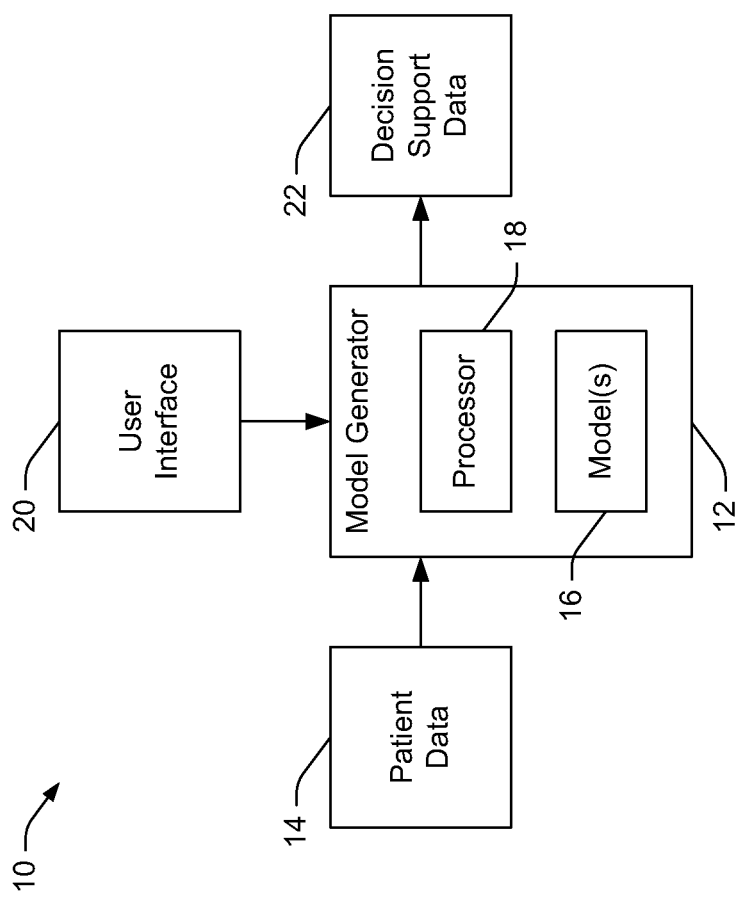
FIG. 1 illustrates a system for generating and utilizing a mathematical model based on patient physiology to run "what-if" scenarios in a clinical setting to assist in medical decision processes, wherein the model provides support for disease diagnosis and treatment planning.
Figure 2:
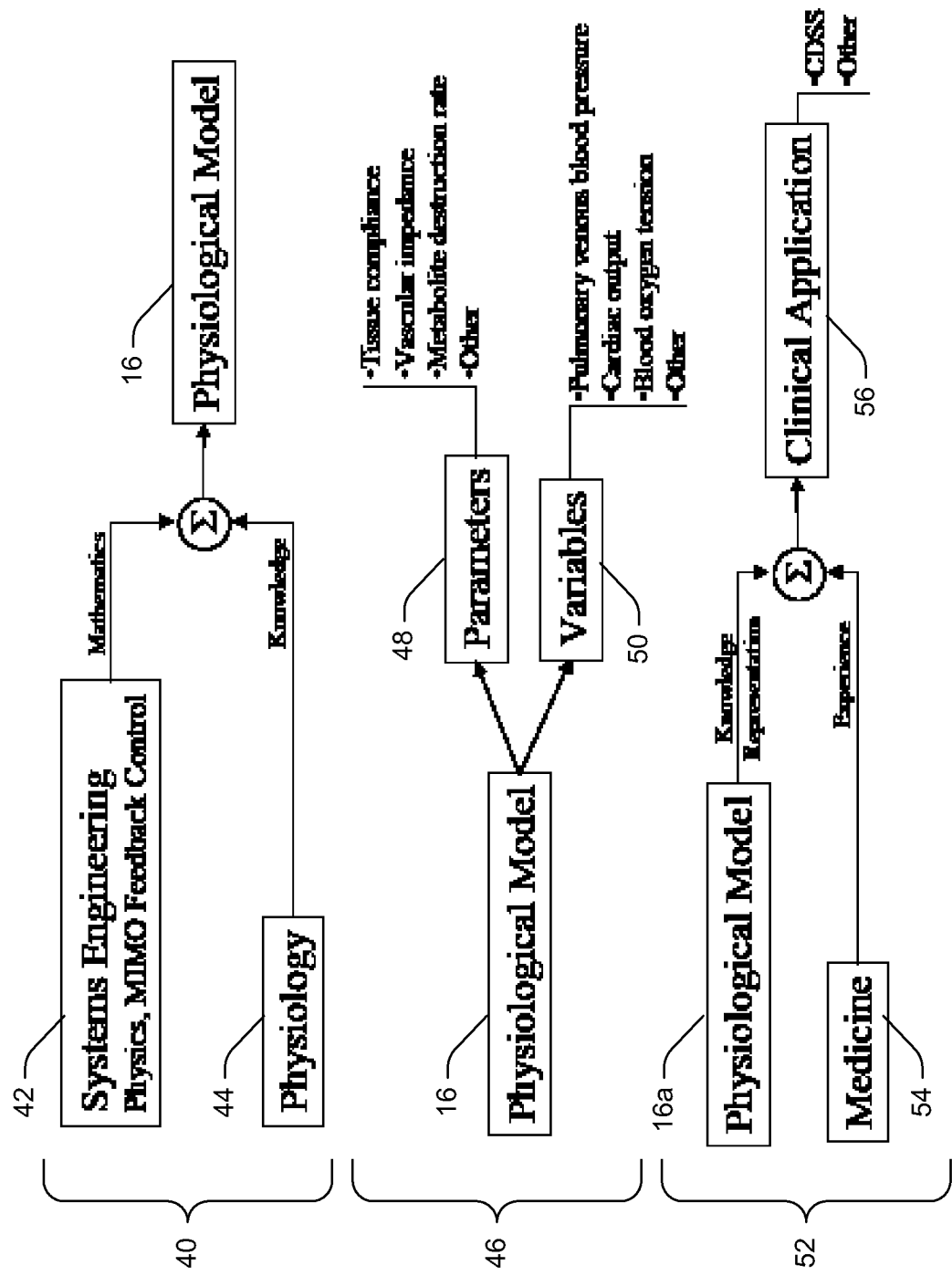
FIG. 2 illustrates an example of physiological model definition and application, such as may be employed in the system of FIG. 1.

FIG. 1 illustrates a system 10 for generating and utilizing a mathematical model based on patient physiology to run "what-if" scenarios in a clinical setting to assist in medical decision processes, wherein the model provides support for disease diagnosis and treatment planning. The system includes a model generator 12, which includes a processor 18, which executes instructions, programs, and/or routines, which are stored on a computer-readable medium (not shown) for building and/or refining pre-generated models 16, which are stored in a database (not shown) or the like. That is, the models 16 are built or pre-generated from physiological data gleaned from a patient population, and are refined by entering new or updated patient data into the pre-generated models 16 to create a refined model 16a (FIG. 2). Model generator 12 receives patient data 14 and inserts it into the one or more pre-generated patient models 16 for a hypothetical test run. The patient data 14 is collected by a vital signs monitor (not shown) or other device that collects patient data. According to one embodiment, the model includes sub-models representing pulmonary circulation, systemic circulation, 4-heart chambers, autonomic nervous system, metabolism, gas exchange, lung mechanism, and/or reflex. A user interface 20 displays relevant cardiopulmonary variables that are reflective of a current health condition of the patient (examples of which are provided below). The user interface 20 permits a user to input parameters for the model(s) 16, in order to adapt the model(s) 16 to a particular hypothetical situation. In one embodiment, the user builds or adjusts a pre-generated model 16 using Simulink (by Mathworks) or another suitable system modeling software application via the user interface. Upon completion of the test run, the model generator outputs decision support data 22 for review by a user, who then applies the decision support data when making a decision related to, for instance, patient treatment or diagnosis. In this manner, a user (e.g., a physician or other clinician) may run simulations of a patient's response to different stimuli using physiological model(s) for a clinical application.

Control system theory and related fields such as systems theory, system identification, and signal processing present powerful mathematical tools capable of representing multi-input multi-output coupled systems in a generalized, numerically stable, and concise way. This formulation can be applied to describing multi-physiological systems that are inherently interlinked having multiple inputs and outputs. Since physiological models describe the actual relevant physiology they are hence deterministic, leaving no factor of stochasticity brought about with statistical or probabilistic methods. This deterministic component adds an element that is missing from conventional mathematical models that are sometimes used in medical diagnosis systems, which rely mostly on collected patient data (statistical) or on knowledge and approximation (inference or probabilistic) approaches. The physiology described in the model(s) 16 is specific to the disease in question, thus facilitating its clinical application. By providing the physician with deterministic physiological information of the patient that serves as support for an eventual clinical decision, from a physiological model that is tailored to the specific patient under diagnosis, decisions regarding patient treatment and diagnosis are significantly improved.

In one embodiment, the user interface 20 includes a model 16 that is output on one or several screens (e.g., on a computer monitor or other user interface), including data related to physiological signals and their behavior over time, as well as averaged over a specified time period. The output model and/or signal behavior information may include: typical variables that physicians deem relevant to a suspected disease (e.g., cancerous growth or tumor, etc.); hard-to-measure (invasive) variables (e.g., cardiac output, etc.); immeasurable (internal) variables that cannot be quantified even with an invasive procedure (e.g., pulmonary circulation, etc.); specific response curves for an emulation that a physician desires to see, such as PV (pressure-volume) loops, etc.; interpretation of results for diagnostic support for a specific disease diagnosis or treatment; knobs or other control means (e.g., touch-screen, buttons, virtual buttons or the like that a user selects using a mouse, stylus, cursor and arrow keys, or other input device, etc.) to modify health conditions, exogenous infusions, corresponding results screens; etc.

According to an example, a physician may be considering ordering a stress test for a patient, but is unsure if the patient's condition is strong enough to endure the stress test. In this scenario, the physiological model(s) 16 is tuned to the patient under question by entering relevant health information such as current condition, disease history, lifestyle, age, gender, body mass index (BMI), etc. E.g., a thrombotic condition entered as part of the patient's health information would be reflected as changes in systemic resistance and compliance in the refined physiology-based model 16a. That is, parameters 48 of the model 16 are adjusted, by for example entering health information specific to the patient (e.g., condition, disease, BMI, etc) so that parameters 48 of the model 16 are effectively updated with, or otherwise reflect new health information specific to the patient. For example, by entering a patient's specific BMI, the tissue compliance, vascular impedance, metabolite destruction rate or other parameters 48 of the model 16 are adjusted to reflect the particular patient's BMI. That is, some parameters are dynamically codependent, such that a patient with a relatively high BMI may be inferred to have different metabolic destruction rate(s), different levels of vascular impedance, etc., than a patient with a relatively low BMI. Accordingly, in the above example, entry of BMI information causes a corresponding adjustment to other parameters that are dynamically linked to the BMI. In this sense, parameter adjustment can be explicit (e.g., direct entry or adjustment of parameter information by a physician or operator) or implicit (e.g., wherein entry or adjustment of a first parameter causes adjustment to other parameters linked to the first parameter). The refined physiological model(s) 16a is then simulated to output vital signs such as heart rate, arterial blood pressure, cardiac output, etc., as continuous temporal signals, or signals averaged over time, as desired by the physician. The resultant decision support data provides the physician with a scenario, as if the patient has undergone the stress test. This consequently provides the physician with information sufficient to support the decision on whether or not the patient can sustain such an exam.

Although many examples presented herein pertain to the cardiovascular system, various features can be extended for other physiological systems, such as respiratory, thermoregulatory, endocrinal, urological, and others, as will be appreciated.

FIG. 2 illustrates an example of physiological model 16 definition and application, such as may be employed in the system 10 of FIG. 1. The upper section 40 shows that a physiological model 16 includes system engineering 42 and knowledge of the human physiology 44 represented mathematically by differential equations. A differential equation describes the dynamic behavior of a system, rather than steady-state only. The middle section 46 shows that such a differential equation (e.g., representing the physiological model 16) is a combination of parameters 48 and variables 50. For instance, parameters 48 include without limitation: tissue compliance, vascular impedance, metabolite destruction rate, etc. Variables 50 include, without limitation: pulmonary venous blood pressure, cardiac output, blood oxygen tension, etc. The bottom section 52 shows that the refined physiology-based model 16a, along with medical clinical experience (medicine 54), allows for use in a clinical setting such as a Clinical Decision Support System (CDSS) or the like, which assists the physician in clinical decisions. Hence, the physiology-based model 16a can run different scenarios simulating a current patient so the physician can decide on an optimal therapeutic plan. Furthermore, the level of detail in the model can vary from molecular to macro-scale, depending on the application.

Figure 3:
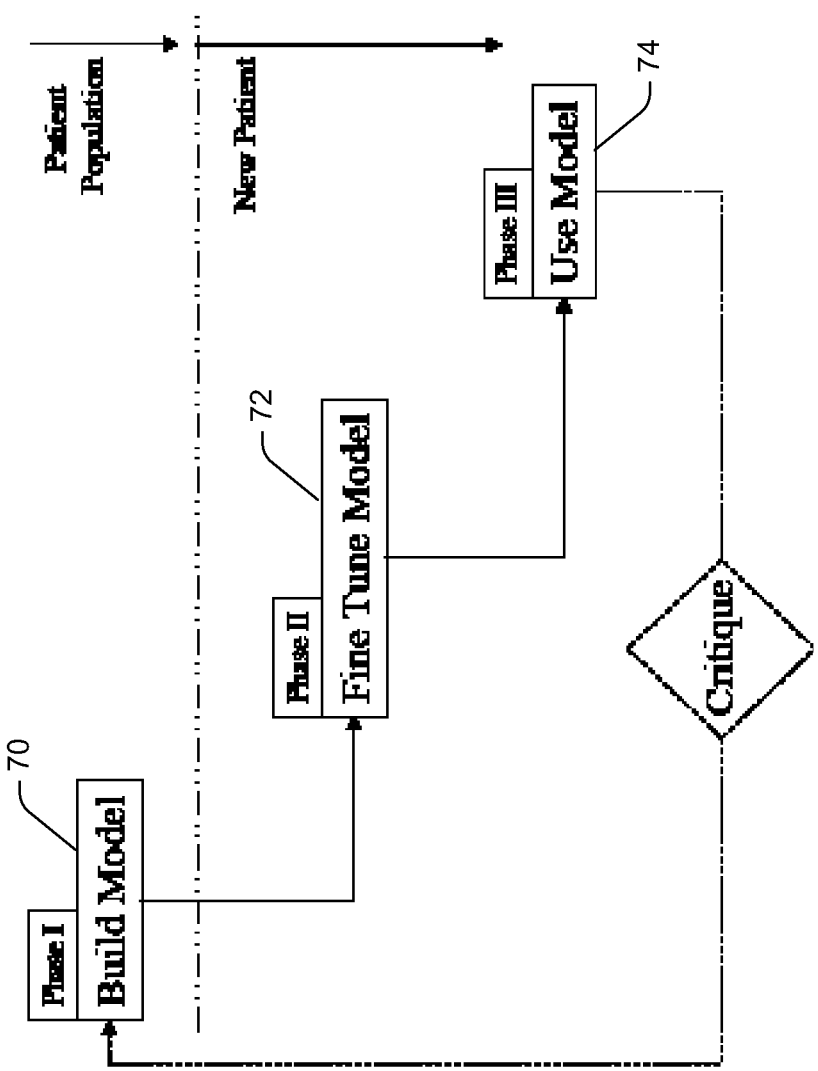
FIG. 3 illustrates three phases of the development and usage of the model.

FIG. 3 illustrates three phases of the development and usage of the model 16. The physiological model 16 is first developed or built, at 70, describing the characteristic of the physiology relevant to a patient system (e.g., the cardiovascular system, the endocrine system, the pulmonary system, the digestive system, etc.). The model 16 can be described by a set of differential equations having parameters as coefficients that multiply the state variables, such as blood pressure, etc., for specific locations of the systemic circulation. Upon studying and selecting the structure of the model (number of terms, including dynamic order and delay,) the mathematical model is first validated with patient data from a large patient population, and the parameters used reflect an average of the patient population. At 72, the model 16 is tuned to the specific patient for which the model 16 is employed by considering health information particular to the patient as already discussed above. At 74, the refined model 16a is employed for the patient, and feedback from the model can be employed, for example, in a next iteration of model generation. For instance, model output can be added to the patient population data to facilitate improving future models.

Figure 4:
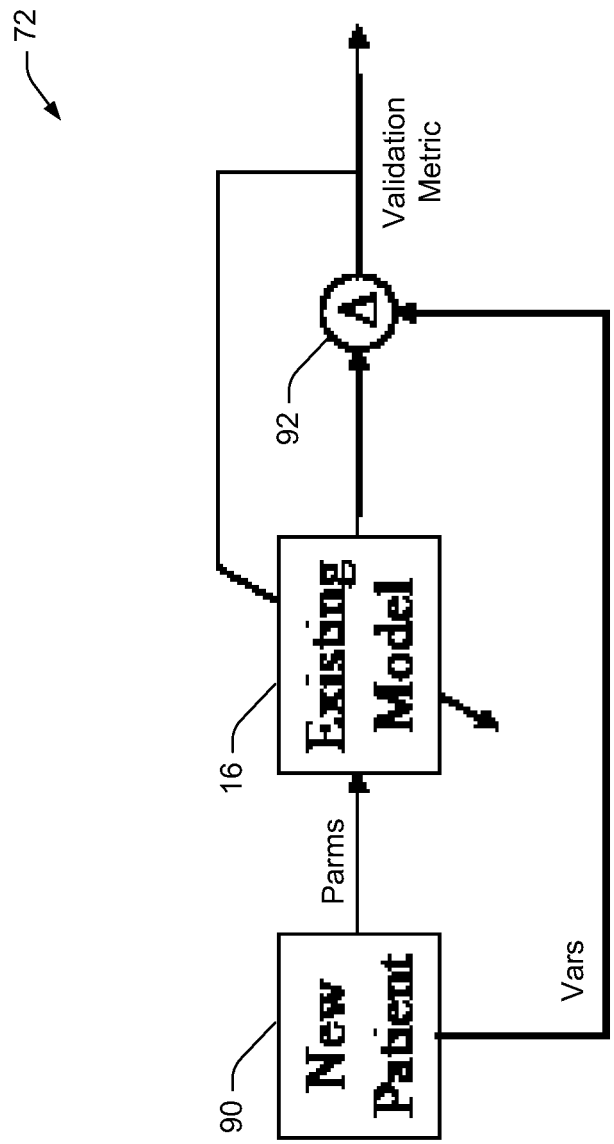
FIG. 4 is a schematic for tuning the model, such as occurs at of FIG. 3.

FIG. 4 is a schematic for tuning the model 16, such as occurs at 72 of FIG. 3. When a new patient 90 is presented to the physician, relevant (e.g., physical) parameter information on that patient is acquired, such as body mass index, etc. Parameters 48 are adjusted or updated based on this acquired patient information. That is, the parameter information is effectively reflected in new updates of the existing parameters 48 of the model 16 (refer to "parms" in FIG. 4), and the mathematical model is tuned or adjusted to the new patient. In one example, entry of BMI data (whether new BMI data or updated BMI data) causes the BMI value(s) in the model 16 to be updated, and also causes adjustment of other, co-related parameter values (e.g., vascular impedance, etc.) that are typically affected by or interdependent on BMI. Such adjustments can be made according to a predefined lookup table, defined as a function of collective patient data employed in pre-generating the model(s) 16, etc., to generate the refined model 16a. This is shown by the oblique arrow in through the existing model 16. If, in addition, the vitals of the patient are taken, then these values can be used to further validate the model. A differentiator 92 determines or identifies the difference between the physiological variables of the real patient, such as vitals and other monitored or known physiological variables, and these same variables' values as predicted by the model. This difference serves as the error criterion for the validation metric.

Figure 5:
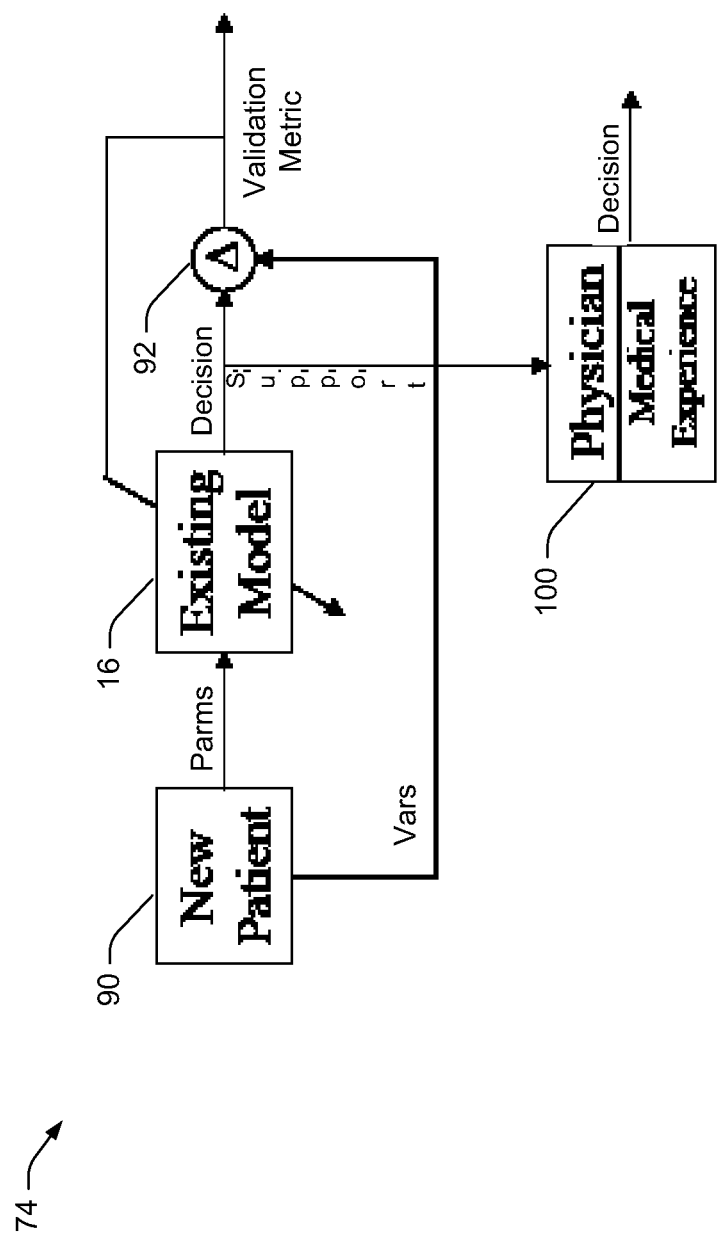
FIG. 5 shows a schematic describing execution of the model by the physician for different scenarios, and simulation of the patient under different cardiovascular conditions, drug and/or exercise effects.

FIG. 5 shows a schematic describing execution of the tuned or refined model 16a by the physician for different scenarios, and simulation of different clinical scenarios involving the patient under different cardiovascular conditions, drug and/or exercise effects. The refined model 16a outputs continuous or periodic temporal signals that can be used to describe the cardiovascular conditions of the patient. The physician, subsequently, uses this information to support their clinical decision on whether or not to order a specific drug or therapeutic test. The physician attends to simulating different clinical scenarios of the patient, e.g. the logical flow from new patient 90 to existing model 16 to physician 100. The physician is not typically involved in the logical steps of variable differentiation and model validation. Furthermore, the feedback link from 74 to 70 in (FIG. 3) can be added whereby the results (e.g., vital signs) can also be used to further tune the population-based model 16 (since the population size has increased by one), in addition to user input from critics (physicians or others), to create a database of physiological models for different classes in patient populations. In this manner, the physiological model gives physiological information that is desired by the physician, but not readily measurable using conventional systems. Examples of such information include pressures in the splanchnic section, pulmonary circulation, cardiac output, ejection fraction, etc., without being limited thereto.

Figure 6:
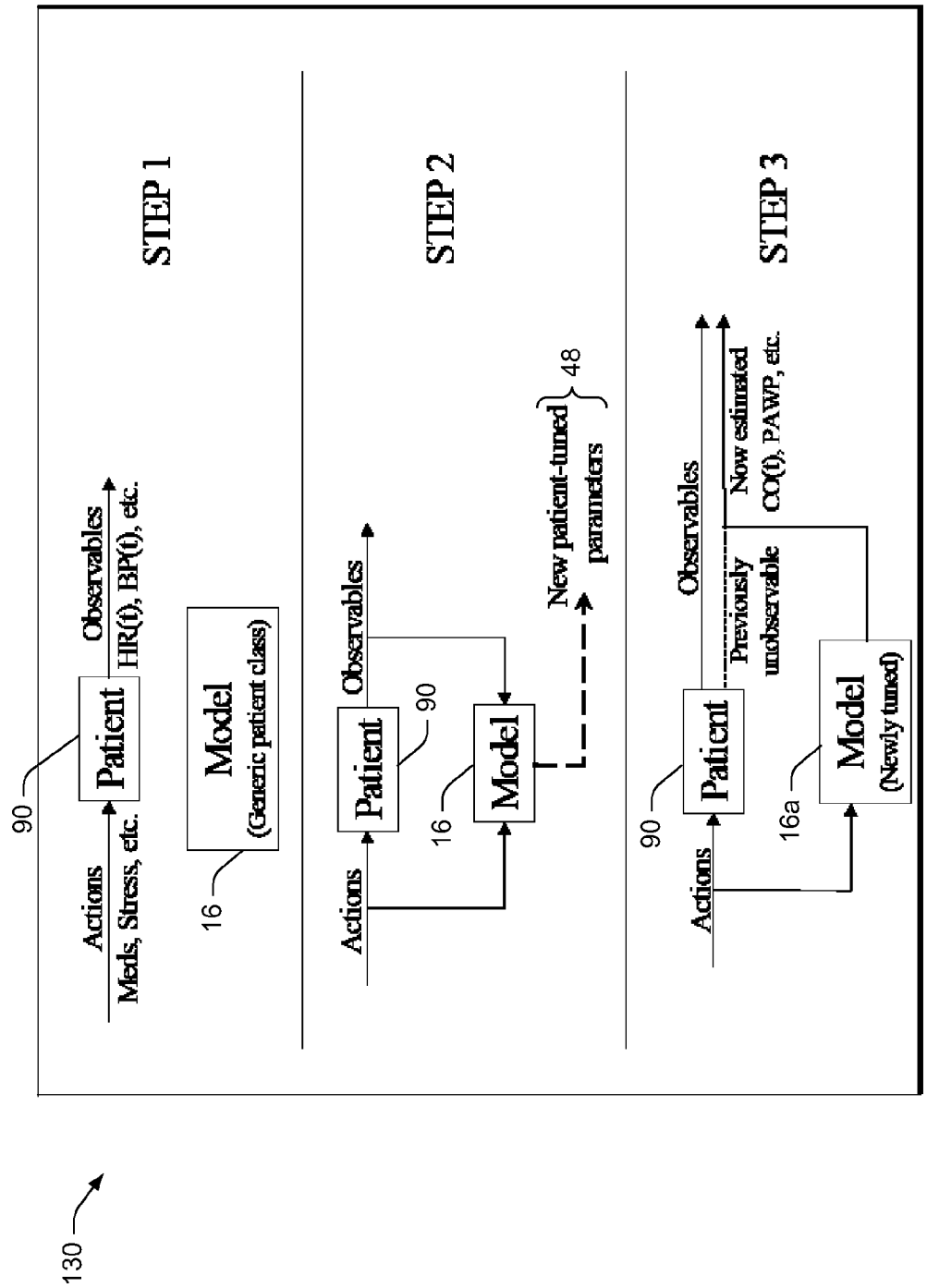
FIG. 6 illustrates a noninvasive method for estimating cardiac output (CO) in a patient.

FIG. 6 illustrates a noninvasive method for estimating cardiac output (CO) in the patient 90. The method relies on two sources of information, including: information already available from observables, such as blood pressure, respiratory rate, heart rate, etc.; and the physiological model 16 of the patient system. In one embodiment, the patient system represented by the model 16 is a cardiovascular system. A physician is presented with a running signal of CO with time, or an average value thereof, on a screen such as the user interface 20 of FIG. 1. A mathematical model 16 that describes the cardiovascular system is developed and validated with normophysiological data, as described in the preceding figures. The model is a system of several ordinary differential equations (ODEs) having parameters that multiply variables and their time derivatives. CO is a variable that is obtained from solving these equations. The parameters in these equations represent physical properties of the cardiovascular system, such as vascular impedance, vessel compliance, myocardium elastance, and the like.

FIG. 6 represents the three steps to be taken in order to perform noninvasive physiological variable estimation. The first step illustrates that the patient has inputs (IV, medications, stress, etc.) and observed outputs (blood pressure, heart rate, respiratory rate, etc.), and the physiological model 16, which is assumed to be validated on the class of patient population that is appropriate for the current patient. For instance, the patient may have the following attributes: elderly, male, smoker. The second step represents a phase wherein observed time signals are fed into a system identification algorithm whereby it computes updates to the existing parameters 48 of the model 16 so that the model is then tuned to the current patient, resulting in model 16a. Step 3 represents an implementation phase of the newly current refined model 16a, which is used to predict physiological variables (also time signals) that are difficult, costly, invasive, (or even impossible) to measure, such as CO(t). The method can be applied in an intensive care unit, emergency room, office, home, etc.

The noninvasively estimated physiological variables are reported as time signals on a screen just as measured variables are presented. In one embodiment, algorithms for variable estimation can be stored on a machine-readable medium and executed by a processor, such as the processor 18 of FIG. 1. Estimated variable output presentation can include cardiac output, ventricular PV diagrams, pulmonary artery wedge pressure (PAWP), and others. For PAWP estimation, the algorithm can first emulate a catheter (e.g. Swan-Ganz) to block the pulmonary artery in order to compute a pulmonary pressure (e.g., immediately after the blockage site). Other variables such as CO and PV information can be obtained in similar manner.

Figure 7:
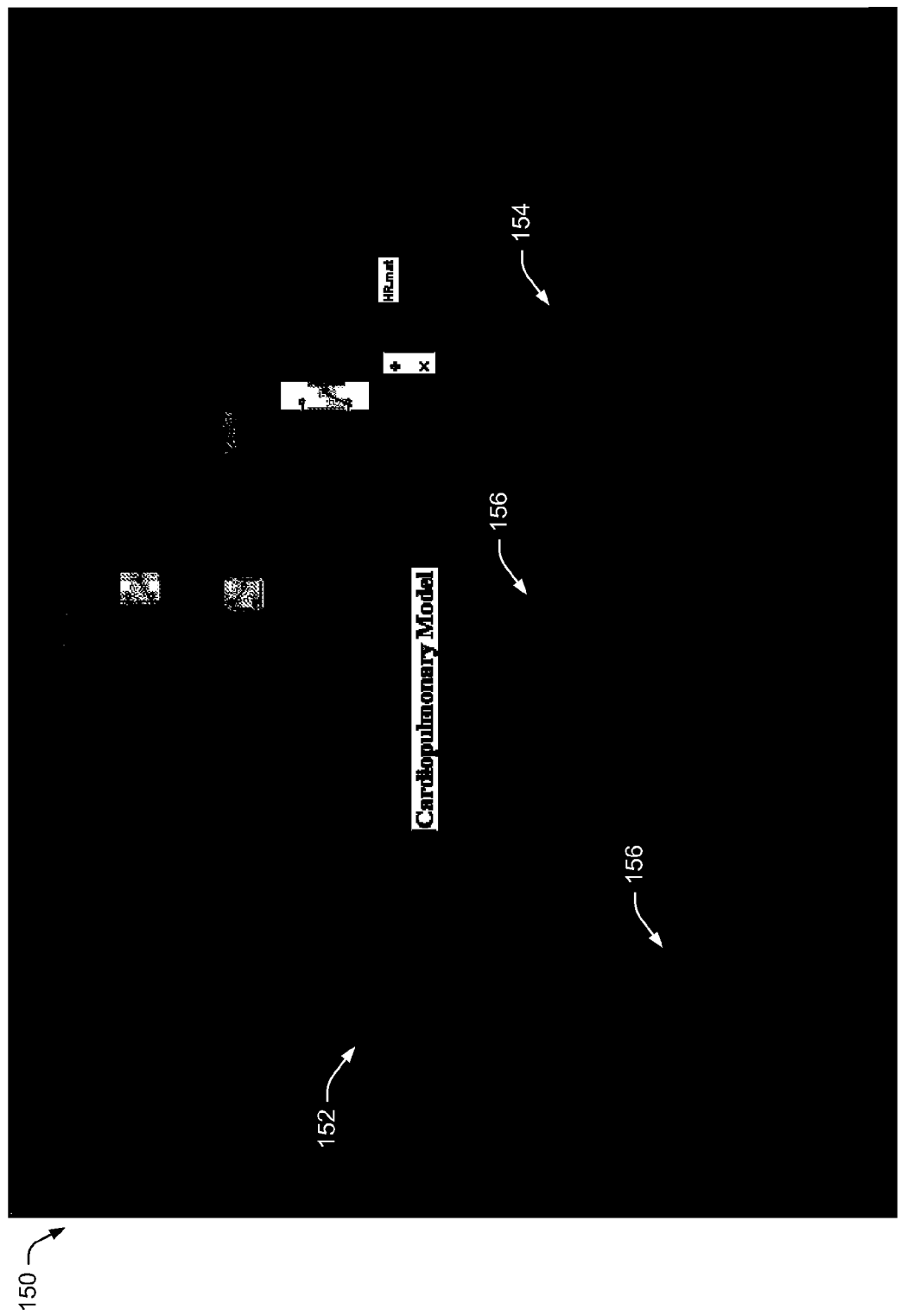
FIG. 7 illustrates an example of a cardiopulmonary model generated using Simulink, by Mathworks.

FIG. 7 illustrates an example of a cardiopulmonary model 150 generated using Simulink, by Mathworks. The model includes several sub-models, representing various model components that are interconnected, such as a gas exchange model 152, a cardiovascular system model 154, etc. Each sub-model includes one or more inputs and one or more outputs, resulting in a multiple-input-multiple-output (MIMO) system model. Additionally, variable inputs and outputs are represented by "tags" 156, for simplification purposes. An operator (e.g., a system designer or physician) can adjust parameters digitally using the model generation software to simulate what-if scenarios or predict CO, etc.

In one embodiment, respective sub-models are isolated and tuned individually, and then recombined. In this manner, system order is reduced for tuning, which permits more rapid tuning. In another embodiment, the larger system model is tuned after recombination of the tuned sub-models.

Figure 8:
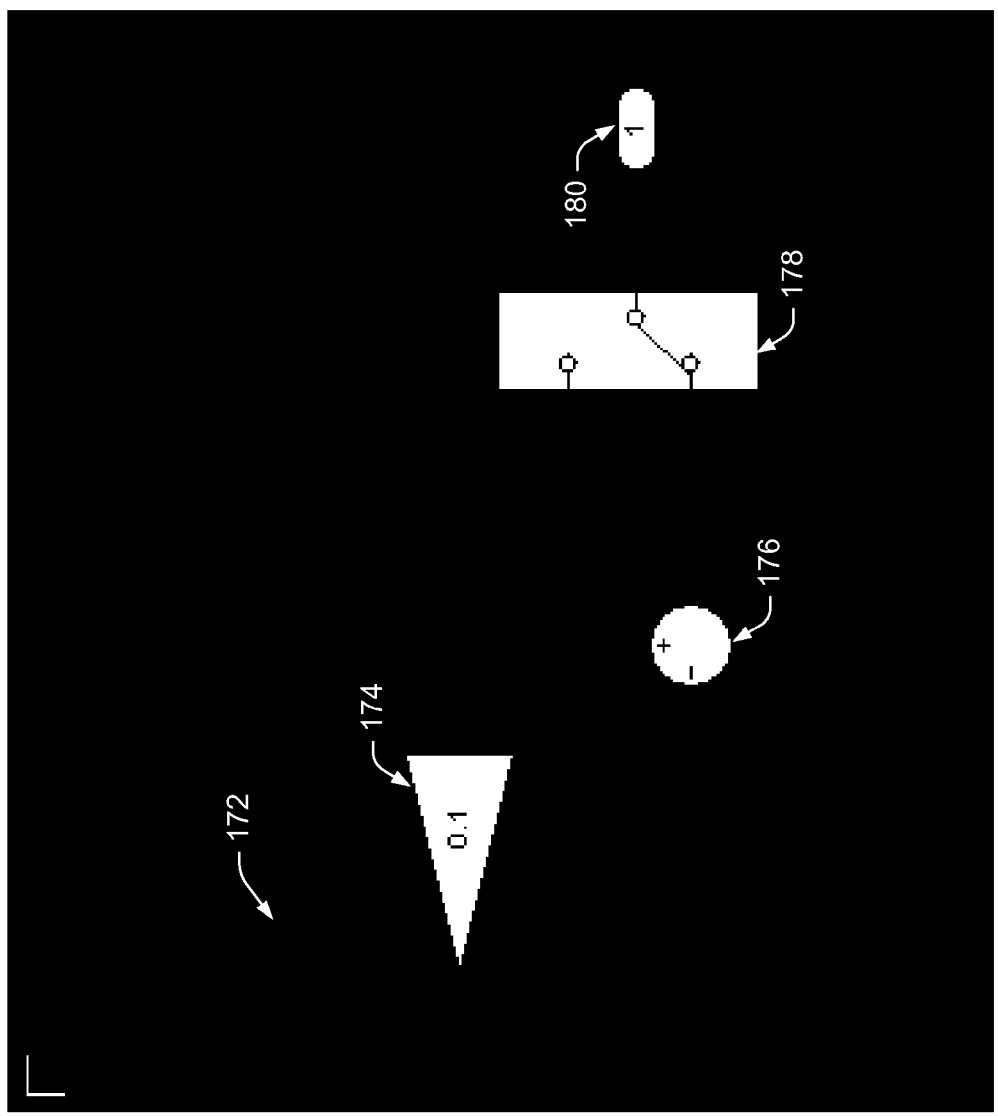
FIG. 8 illustrates an example of a hypovolemic shock simulation model that receives as input a patient variable.

FIG. 8 illustrates an example of a hypovolemic shock simulation model 170 that receives as input a patient variable 172. In this example the patient variable is total blood volume (Vt). The value Vt is input to a positive terminal of a gain/amplifier 174 representing blood loss and concurrently into a subtractor 176. In this case, the amplifier has a value of 0.1, indicating that 10% of Vt is lost during each pass (e.g., each pulse of from the source Vt). The output of the amplifier is fed into a negative terminal of the subtractor, to simulate blood lost from the total volume Vt. Output from the subtractor is fed into a first terminal of a hypovolemic shock switch 178, and the volume Vt is fed into a second terminal of the switch. A reduced volume Vt1 180 is output from the switch, and used as a total starting volume in a second iteration of the model. Other shock scenarios such as cardiogenic and obstructive can be similarly simulated.

The innovation has been described with reference to several embodiments. Modifications and alterations may occur to others upon reading and understanding the preceding detailed description. It is intended that the innovation be construed as including all such modifications and alterations insofar as they come within the spirit or scope of the appended claims or the equivalents thereof.

Having thus described the various embodiments, the invention is now claimed to be:

1. A non-transitory computer readable medium comprising a program that is configured to emulate cardiopulmonary function of a patient comprising computer-executable instructions for:
providing a generic model of the cardiopulmonary system of the patient, said model including pulmonary circulation, systemic circulation, 4-heart chambers, autonomic nervous system, metabolism, gas exchange, lung mechanism, and reflex;
measuring cardiopulmonary variables of the patient;
displaying relevant cardiopulmonary variables that are reflective of a current health condition of the patient;
simulating functioning of the cardiopulmonary system;
receiving patient data and inserting the patient data into the model;
representing the model as a plurality of interrelated differential equations that are solved to determine expected values for the cardiopulmonary variables; and
comparing the expected values to measured values of the cardiopulmonary variables to determine a difference there between;
outputting decision support data for consideration by a user when diagnosing or treating the patient; and
feeding the decision support data back into the model to update the model and include the patient in a patient population for future model simulations.

2. The computer-readable medium of claim 1, the program further comprising:
refining the model as a function of the difference between the expected and measured cardiopulmonary variable values.

3. A program embodied on a non-transitory computer readable medium that is configured to emulate the cardiopulmonary functioning of a patient, the program comprising computer-executable instructions for:
providing a generic model of the cardiopulmonary system of the patient;
measuring cardiopulmonary variables of the patient;
iteratively changing cardiopulmonary parameters of the model in order for cardiopulmonary variables of the generic model to reflect the cardiopulmonary variables of the patient;
receiving patient data and inserting the patient data into the model;
representing the generic model as a plurality of interlinked differential equations including the cardiopulmonary parameter and variables, and solving for the variables during a hypothetical clinical simulation;
comparing the expected values to measured values of the cardiopulmonary variables to determine a difference there between;
outputting decision support data for consideration by a user when diagnosing or treating the patient; and
feeding the decision support data back into the model to update the model and include the patient in a patient population for future model simulations.

4. A clinical patient modeling system, including:
a pre-generated physiological model of a patient, comprising at least one sub-model of a physiological system in a patient with a plurality of differential equations that describe relationships among physiological parameters and variables relevant to the physiological system, wherein the model is stored on a non-transitory computer-readable medium;
a processor that executes an algorithm that solves the differential equations for at least one variable and outputs the results as part of the decision support data, wherein the processor compares the at least one solved variable to an expected value therefor, and determines a difference there between to generate a validation metric that validates the model;
a model generator configured to receive patient data, insert the patient data into the physiological model, and output decision support data for consideration by a user when diagnosing or treating the patient; and
a user interface configured to receive one or more parameters to adapt the model to a hypothetical situation into which the user is considering placing a patient;
wherein the decision support data is fed back into the model to update the model and include the patient in the patient population for future hypothetical model simulations.

5. The system according to claim 4, wherein the physiological model comprises known physiological data from a patient population, represented by the differential equations.

6. The system according to claim 4, wherein the parameters include at least one of tissue compliance, vascular impedance, or metabolite destruction rate.

7. The system according to claim 4, wherein the variables include at least one of cardiac output, blood oxygen tension, or pulmonary venous blood pressure.

8. The system according to claim 4, wherein the model generator refines the model in response to parameter information entered via the user interface.

9. The system according to claim 4, further comprising a plurality of interrelated, interacting models.

10. The system according to claim 4, wherein the at least one sub-model is a model of at least one of a pulmonary system, a cardiovascular system, a metabolic system, a renal system, an endocrine system, a reproductive system, or a hepatic system.

11. A method for performing patient model analysis, including:
    generating, via a processor, the model from physiological data gleaned from a patient population;
    displaying the model on a user interface;
    representing the physiological data in the model as differential equations that describe parameters and variables associated with the patient;
    adjusting parameters in the model as a function of parameter information entered via the user interface to adjust the model for the hypothetical situation into which the patient is to be placed:
    running a simulation on the model to generate decision support data and solve for the variables in the model to determine expected values for the variables;
    comparing the expected values to measured values of the variables to determine a difference there between;
    feeding the decision support data back into the model to update and refine the model and include the patient in the patient population for future hypothetical model simulations; and
    outputting the refined model on the user interface.

12. A method of evaluating hypothetical clinical scenarios, including:
    generating, via a processor, a model from physiological data gleaned from a patient population;
    representing the physiological data in the model as differential equations that describe parameters and variables associated with a patient;
    adjusting parameters in the model to adapt the model for a hypothetical situation into which the patient is to be placed;
    running a simulation on the model to generate decision support data and solve for the variables in the model to determine expected values for the variables;
    comparing the expected values to measured values of the variables to determine a difference there between:
    refining the model in response to parameter information entered via the user interface to generate a refined model, and feeding the decision support data back into the model to update and refine the model and include the patient in the patient population for future hypothetical model simulations; and
    outputting the refined model on the user interface.

13. The method according to claim 12, further including the at least one solved variable to an expected value therefor, and determines a difference therebetween to generate a validation metric that validates the model.

14. The method according to claim 12, further including a plurality of inter-related, interacting models.

15. The method according to claim 12, wherein the physiological model comprises known physiological data from a patient population, represented by the differential equations.

16. The method according to claim 12, wherein the parameters include at least one of tissue compliance, vascular impedance, and metabolite destruction rate.

17. The method according to claim 12, wherein the variables include at least one of cardiac output, blood oxygen tension, and pulmonary venous blood pressure.

18. The method according to claim 12, wherein the at least one sub-model is a model of at least one of a pulmonary system, a cardiovascular system, a gastrointestinal system, a renal system, an endocrine system, a reproductive system, a gas-exchange system, or a hepatic system.

19. A processor or non-transitory computer-readable medium programmed to execute computer executable instructions for:
    generating a model from physiological data gleaned from a patient population;
    representing the physiological data in the model as differential equations that describe parameters and variables associated with a patient;
    adjusting parameters in the model to adapt the model for a hypothetical situation into which the patient is to be placed;
    running a simulation on the model to generate decision support data and solve for the variables in the model to determine expected values for the variables;
    comparing the expected values to measured values of the variables to determine a difference there between
    refining the model in response to parameter information entered via the user interface to generate a refined model, and feeding the decision support data back into the model to update and refine the model and include the patient in the patient population for future hypothetical model simulations; and
    outputting the refined model on the user interface.

* * * * *